United States Patent [19]

Chakraborty et al.

[11] Patent Number: 5,550,022
[45] Date of Patent: Aug. 27, 1996

[54] METHOD FOR THE DETERMINATION OF PATHOGENIC LISTERIA BACTERIA

[75] Inventors: Trinad Chakraborty, Würzburg; Werner Goebel, Veitshöchheim, both of Germany; Servatius H. W. Notermans, Bilthoven, Netherlands

[73] Assignee: Boehringer Mannheim GmbH, Mannheim, Germany

[21] Appl. No.: 303,577

[22] Filed: Sep. 8, 1994

Related U.S. Application Data

[63] Continuation of Ser. No. 10,512, Jan. 28, 1993, abandoned, which is a continuation of Ser. No. 573,214, Oct. 15, 1990, abandoned.

[30] Foreign Application Priority Data

Jan. 19, 1989 [DE] Germany .......................... 39 01 397.9
Mar. 3, 1989 [DE] Germany .......................... 39 06 832.3

[51] Int. Cl.$^6$ ................. C12Q 1/68; C07H 21/04
[52] U.S. Cl. .................. 435/6; 536/23.1; 536/24.32
[58] Field of Search ................. 435/6; 536/23.1, 536/24.32

[56] References Cited

U.S. PATENT DOCUMENTS

| | | | |
|---|---|---|---|
| 4,950,589 | 8/1990 | Butman et al. | 435/7 |
| 5,089,386 | 2/1992 | Stackebrandt et al. | 435/6 |

OTHER PUBLICATIONS

Hames et al Nucleic Acid Hybridization: a practical approach (IRL Press) (1985) pp. 80–81.
Devereux et al. Nucl Acids Res, (1984) 12(1) 387–395.
Bakulov et al. Biosis Abstract No. 87078358 Mol Genet Mikrobiol Virusol 0(7) 1988, 31–35.
Datta et al. Appl. Envir Microb. (1987) 53(9) 2256–59.

*Primary Examiner*—W. Gary Jones
*Assistant Examiner*—Ethan Whisenant
*Attorney, Agent, or Firm*—Felfe & Lynch

[57] ABSTRACT

Nucleic acids which preferably hybridize under the hybridization conditions 5–6× SSC and 42° C. to 60° C. with a 2.5 kb large KpnI-BamHI fragment from pLM63, preferably with a nucleic acid according to FIG. 1. Such nucleic acids are suitable for hybridization tests for Listeria bacteria if they contain reporter groups. Proteins are also described which are suitable for the production of antibodies against Listeria bacteria.

10 Claims, 4 Drawing Sheets

Figure 1-1

NUCLEOTIDE SEQUENCE OF PLASMID pPLM63

```
        10        20        30        40        50        60
         |         |         |         |         |         |
CTTTTCATTTAGATAAAACAAAAGAAGAAATTGGCGCTTTACCTGCTTCGGCGATTGAAT
  PheHisLeuAspLysThrLysGluGluIleGlyAlaLeuProAlaSerAlaIleGluCys 70        80        90       100       110       120
         |         |         |         |         |         |
GTCAGTATGAGGCTTTTGTGATTAATGAAGCCAATAATTAAGGAGTGATAAAATGCAGGT
  GlnTyrGluAlaPheValIleAsnGluAlaAsnAsn---           METGlnVal
                                                   ↳ Protein III
       130       140       150       160       170       180
         |         |         |         |         |         |
TTTAGTTTTACCAGAAAATAAGGATATCAATTATATAAAAACGGTCCAAGAAGTAAAACG
  LeuValLeuProGluAsnLysAspIleAsnTyrIleLysThrValGlnGluValLysArg 190       200       210       220       230       240
         |         |         |         |         |         |
ATTTTTTGCGGATTTTGAGCGGTTTCGGATGATTACGGGGTTATCAAAAAAGCCACATTT
  PhePheAlaAspPheGluArgPheArgMETIleThrGlyLeuSerLysLysProHisLeu 250       260       270       280       290       300
         |         |         |         |         |         |
ACTTAGAAATGGTTTTCTGGAAGAGCCGCAGTTTGAGCCGGTAGCATTTTCTGCTAGACA
  LeuArgAsnGlyPheLeuGluGluProGlnPheGluProValAlaPheSerAlaArgHis 310       320       330       340       350       360
         |         |         |         |         |         |
TAATAAAGAAGTCATTTTGGAAGCGCGATGGTTGGTAGAGAAATATACTGAAATGTTGAA
  AsnLysGluValIleLeuGluAlaArgTrpLeuValGluLysTyrThrGluMETLeuAsn 370       380       390       400       410       420
         |         |         |         |         |         |
TCAGATGGATGATTTATATCGAACTATTTTGATGGAATGTTACGTGGAACGAAAACAAGA
  GlnMETAspAspLeuTyrArgThrIleLeuMETGluCysTyrValGluArgLysGlnAsp 430       440       450       460       470       480
         |         |         |         |         |         |
TGTGGCGGTAATGATGGATTTACCGTATGAAATTGCCCAGTTTAAACGGATAAAAAAACG
  ValAlaValMETMETAspLeuProTyrGluIleAlaGlnPheLysArgIleLysLysArg 490       500       510       520       530       540
         |         |         |         |         |         |
GGCAGTGCTAGAACTTGCAACGCTAATGGGGATTTTAGTAAGGAAATGATGATACTTTCG
  AlaValLeuGluLeuAlaThrLeuMETGlyIleLeuValArgLys---
                                       ——→ Protein III
```

Figure 1-2

```
         550       560       570       580       590       600
          |         |         |         |         |         |
TGATATTTTGAAACATCATTTTCCTATTAATATAGAAGTAAGCTAATTGTCCAGTAAGCG 610       620       630       640       650       660
          |         |         |         |         |         |
GATGACAATAAAAGCTGCATCAGAATGAAGGTGCACCGATTTTCTGATAATACATGATGT 670       680       690       700       710       720
          |         |         |         |         |         |
TTTACAAGGAATTTGTTTTTATGATTGGATTTAAATCCGTTGAGATAAACAAATATTCTA 730       740       750       760       770       780
          |         |         |         |         |         |
TTTTGGAAAGTAAAGTTCGGAGGAATAAATTATTAAATGTGGTCTTGACCGAACTTTGCT 790       800       810       820       830       840
          |         |         |         |         |         |
TTCTGTTTTAAAGGAGTGAACGTTTGGTGAAGAGTTTGAGCTTCATGAGAGTTTTGGAAG
                              ValLysSerLeuSerPheMETArgValLeuGluAla
                                         ↳→ Protein I 850       860       870       880       890       900
          |         |         |         |         |         |
CAGTGAGAACAATGCTCCAGGAAAAAGGCGGACTAGATATTTCTATTGTAATGCGTGACC
ValArgThrMETLeuGlnGluLysGlyGlyLeuAspIleSerIleValMETArgAspGln 910       920       930       940       950       960
          |         |         |         |         |         |
AAGTGGAAATGCCTACAACGATGATCGAGATGATTGATCAAGAGGAAGAAGAAAGCCAAA
ValGluMETProThrThrMETIleGluMETIleAspGlnGluGluGluGluSerGlnThr 970       980       990      1000      1010      1020
          |         |         |         |         |         |
CTGCCTGGAAAGAAAAATACCGTTTTGCAATCCATCATTATACAAATGAAACGGACTTAG
AlaTrpLysGluLysTyrArgPheAlaIleHisHisTyrThrAsnGluThrAspLeuAla 1030      1040      1050      1060      1070      1080
          |         |         |         |         |         |
CGGGAGTCGAAAAGATAGATACGCTTATCCAAACAGGATTCACTTTGCCTGAAGGATACA
GlyValGluLysIleAspThrLeuIleGlnThrGlyPheThrLeuProGluGlyTyrLys 1090      1100      1110      1120      1130      1140
          |         |         |         |         |         |
AATTAATCGCTGTTCGACATTACGGAAAACAAAATTTAGTCAAAGAAAATACGTTAATTC
LeuIleAlaValArgHisTyrGlyLysGlnAsnLeuValLysGluAsnThrLeuIleHis
```

Figure 1-3

```
        1150      1160      1170      1180      1190      1200
          |         |         |         |         |         |
ACGCAAAAACCAGTTTTGAAGTAAGTATTTGTCGTGAATTAAAAGTAAAAATTTAGGGGG
  AlaLysThrSerPheGluValSerIleCysArgGluLeuLysValLysIle---
                                          ————▶ Protein I 1210      1220      1230      1240      1250      1260
          |         |         |         |         |         |
AAATATTAATGGCATTTGAAGAGAATTTATATTGTGATTATACACCGGGAGCTGCTAAAG
        (METAlaPheGluGluAsnLeuTyrCysAspTyrThrProGlyAlaAlaLysAla
         └──▶ Protein II 1270      1280      1290      1300      1310      1320
          |         |         |         |         |         |
CGGTCGCGGGGAAAGATGTAATTTTAGCAGTTTTTAACGCAGCGGGGGACAAACTATTAG
  ValAlaGlyLysAspValIleLeuAlaValPheAsnAlaAlaGlyAspLysLeuLeuAla 1330      1340      1350      1360      1370      1380
          |         |         |         |         |         |
CGGTTGCGGGCCAACAAGGTCTAACTGTAAACCGTTCTAAAGATAGCATTGAAATTACAT
  ValAlaGlyGlnGlnGlyLeuThrValAsnArgSerLysAspSerIleGluIleThrSer 1390      1400      1410      1420      1430      1440
          |         |         |         |         |         |
CTAAAGATACAGTTGGCGGATGGAAATCCAAAATTGGCGGTATGAAAGAATGGTCAATTG
  LysAspThrValGlyGlyTrpLysSerLysIleGlyGlyMETLysGluTrpSerIleGlu 1450      1460      1470      1480      1490      1500
          |         |         |         |         |         |
AAAATGACGGATTATATGTCGCTGATGCAGAGTCTCACAAAGAATTGGCGAAATATTTCG
  AsnAspGlyLeuTyrValAlaAspAlaGluSerHisLysGluLeuAlaLysTyrPheGlu 1510      1520      1530      1540      1550      1560
          |         |         |         |         |         |
AAAGTGATAGCCCGGTTTGTGTGAAAATCATTAATCAAGCATCTAAAAAAGGTCTTTTCG
  SerAspSerProValCysValLysIleIleAsnGlnAlaSerLysLysGlyLeuPheGly 1570      1580      1590      1600      1610      1620
          |         |         |         |         |         |
GTGGTTTGGCAATTGTAGCTGACTATAGTTTTGAAGCACCTTTTGACGAAGCGATGACTT
  GlyLeuAlaIleValAlaAspTyrSerPheGluAlaProPheAspGluAlaMETThrTyr 1630      1640      1650      1660      1670      1680
          |         |         |         |         |         |
ACTCTGTAAAACTAGACGGAATGGGCGCGCTTGTTGATTTAACGATTACTGAGGGCGGCG
  SerValLysLeuAspGlyMETGlyAlaLeuValAspLeuThrIleThrGluGlyGlyAsp 1690      1700      1710      1720      1730      1740
          |         |         |         |         |         |
ACCAAATGCCCGGCGAAACACCTGTAGCACCAGCAGAATAAAATAGAAAGCCACTGAAAT
  GlnMETProGlyGluThrProValAlaProAlaGlu---
         ————▶ Protein II
```

Figure 1-4

```
         1750        1760        1770        1780        1790        1800
          |           |           |           |           |           |
AAGTGGCTTTCCCTTAGGAGGAAAATAAATGTTTGAAGTGAATGATACAACTTATATTTT
                                 METPheGluValAsnAspThrThrTyrIleLeu 1810        1820        1830        1840        1850        1860
          |           |           |           |           |           |
ACGATTTAATAAACAAAAAGTTAAAACGGTGGAATTAACATCAGGGATTAGTTTAGTTGC
ArgPheAsnLysGlnLysValLysThrValGluLeuThrSerGlyIleSerLeuValAla 1870        1880        1890
          |           |           |
AGCTTTGACTGCGAATAAAGGGATTTTGAG
AlaLeuThrAlaAsnLysGlyIleLeu
```

METHOD FOR THE DETERMINATION OF PATHOGENIC LISTERIA BACTERIA

This application is a continuation of application Ser. No. 08/010,512, filed Jan. 28, 1993, now abandoned, which is a continuation of Ser. No. 07/573,214, filed Oct. 15, 1990, now abandoned.

BACKGROUND OF THE INVENTION

The invention concerns a method for the determination of pathogenic Listeria bacteria, a nucleic acid probe, as well as a protein which is suitable for the production of antibodies against pathogenic Listeria bacteria.

Listeria are a heterogeneous group of gram-positive bacteria and consist essentially of the species *Listeria monocytogenes, L. innocua, L. welshimeri, L. seeligeri, L. ivanovii, L. grayi* and *L. murrayi*. Only two of these species are pathogenic, namely *L. monocytogenes* for humans and animals and *L. ivanovii* for animals. Listeriosis usually manifests itself in humans as a bacterial meningitis and septicaemia as well as miscarriages and stillbirths in pregnant women. In sheep and cattle listeriosis manifests itself as miscarriage, encephalitis, septicaemia and mastitis. (N. Engl. J. Med. 308 (1983), 203–206, J. Infec. 15 (1987), 165–168, Linnan, M. J. et al., An investigation of listeriosis in Southern California 1985, in Courtieu, A. L. et al., (eds) Listeriose, Listeria, Listeriosis 1985–1986, University of Nantes).

Recently an increasing number of listeriosis diseases have been observed in humans, the cause of which is regarded to be due to the contamination of milk and cheese, above all soft cheese varieties, by Listeria bacteria. Therefore an examination of food for Listeria contamination is important and is obligatory for cheese in the USA.

A method for the determination of Listeria monocytogenes is known from Int. J. Food Microbiol. 4 (1987), 249–256 in which the microorganism is enriched selectively in a liquid medium at 4° C., cultured on special agar plates and subsequently the biotype and serotype determined by a multitude of biochemical tests. This method is very laborious and time-consuming and it takes 14 days and longer before the end result is available. In addition the assessment is very difficult to carry out and is not suitable for routine investigation.

A method for the determination of Listeria bacteria is known from Appl. Environ. Microbiol. 53 (1987), 2256–2259 which is carried out by colony-hybridization with radioactively labelled DNA probes. Colony-hybridization in itself would be a suitable method for a rapid and simple analysis of the contamination of food by Listeria bacteria. However, a nucleic acid probe is necessary for this which hybridizes with all pathogenic Listeria bacteria (*L. monocytogenes* and *L. ivanovii*) but not with the other Listeria bacteria. DNA probes known up to now (listeriolysin 0, β-listeriolysin; cf. Infection and Immunity 55 (1987), 3225–3227 and Applied Environmental, Microbiology 53 (1987), 2256–2259) are too non-specific and therefore result in an unacceptable number of false positive and false negative results.

The object of the present invention is therefore to provide a nucleic acid with which specific hybridization tests for pathogenic Listeria bacteria are possible as well as proteins derived from this which are suitable as immunogens for the production of antibodies against pathogenic Listeria bacteria.

BRIEF DESCRIPTION OF THE DRAWING

FIG. 1 shows the nucleotide sequence of plasmid pPLM63 and the amino acid sequence of the protein for which the sequence encodes.

THE INVENTION

This object is achieved by a nucleic acid which hybridizes, preferably within an hour, with the 2.5 kb large KpnI-BamHI fragment from the plasmid pLM63 (DSM 5220) under the hybridizing conditions 5–6× SSC and 42°–60° C. The nucleic acid is preferably at least 27 nucleotides long. A nucleic acid is likewise preferred which hybridizes under these conditions with the nucleic acid sequence according to FIG. 1 (nucleotide sequence of plasmid pPLM63, contained in the above mentioned fragment. A nucleic acid is likewise preferred which hybridizes under these conditions with the nucleic acid corresponding to nucleotides 822–1890 of FIG. 1. It is particularly preferable to use the nucleic acid with the sequence according to FIG. 1, a fragment of this sequence from nucleotide 1–714, 822–1890, 935–1244, from 1158–1185 or from 1209–1718 or a fragment of the sequence according to FIG. 1 of at least 27 nucleotides length. The maximum length of the probe is not critical. Usually it should not considerably exceed the length of the pLM63 fragment i.e. 2.5 kb.

In the sense of the invention nucleic acids are understood as oligodeoxyribonucleosides or the corresponding oligoribonucleosides as well as their derivatives which are suitable for hybridization.

The Listeria test is carried out by molecular biological techniques familiar to the expert involving DNA/DNA, RNA/RNA or RNA/DNA hybridization for the detection of homologous nucleic acid sequences. For this the methods of colony or plaque hybridization and blotting procedures (e.g. Southern blot and dot blot) are usually used. Further known procedures are described in U.S. Pat. No. 4,358,535, Gene 21 (1983) 7785, EP-B 130515, EP-B 70685, EP-B 70687 and EP-A 238332.

The labelling of the probe is carried out for example with radioactive derivatized deoxyribonucleoside triphosphates, non-radioactively with biotin, avidin, streptavidin, a fluorescent dye or a hapten. In the latter case the detection of the product of hybridization is carried out by the determination of the enzymatic activity of the marker enzyme in an anti-hapten-antibody-enzyme conjugate via coupled dye systems. Further procedures are for example described in DE-A 38 13 278 and DE-A 38 00 644. The substance with which the probe is labelled is also denoted there as reporter group.

The method in accordance with the present invention is preferably carried out by labelling the nucleic acid according to the present invention radioactively, or with biotin, streptavidin, avidin or with a hapten and subsequently hybridizing and determining the label.

Various methods can be applied to label the probes according to the present invention as described for example in Molecular Cloning, Maniatis et al (1982), Cold Spring Harbor Laboratory, Cold Spring Harbor, New York. The incorporation of biotin in nucleic acids is described for example in PNAS USA 78 (1981) 6633 and PNAS USA 79 (1982) 7331. A further method for the incorporation of reporter groups is described in EP-A 292128.

The radioactive labelling can be carried out according to the known procedures. The incorporation of a hapten can be carried out for example enzymatically, chemically or photochemically. The preparation of the oligonucleotide probes can for example be carried out according to the "random-primed" method (Anal. Biochem. 132 (1983) 6) the "specific-primed" method, the "reverse transcription" method (Stelow, J. K. and Hollander A. Eds, Genetic Engineering, Plenum Press New York and London, Vol. 1, page 1), according to the "fill in" or "nick-translation" method (J. Mol. Biol. 113 (1977) 237), the "tailing" method, the "transcription" method (J. Mol. Biol. 166 (1983) 477), the photochemical method (Nucl. Acids Res. 13 (1985) 745–761), or be carried out chemically. These methods are for example described in more detail in DE-A 38 13 278.

The material to be examined (sample) is prepared in the usual way before the determination is carried out. In this process it is preferable to isolate the RNA and/or DNA from the sample according to known procedures (cf. e.g. Maniatis, Molecular Cloning (1982) 280–281).

Before carrying out the determination, the nucleic acids of the sample can be cleaved into shorter fragments. This can be effected for example by ultrasonic treatment, treatment with microwaves or treatment with restriction endonucleases. In case the samples contain double-stranded nucleic acids, these must be separated into single strands before the determination is carried out. This can be carried out by methods familiar to the expert by denaturation (e.g. heat treatment or treatment with alkali).

The derivatized or radioactively labelled nucleic acid probe is brought into contact with denatured DNA or RNA of the sample to be examined which is bound to a carrier and in doing this temperature, ionic strength, pH value, buffer, and other conditions are so chosen that, depending on the length of the nucleic acid probe and the resulting melting temperature of the expected hybrid, the labelled nucleic acid can bind to homologous nucleic acids (J. Mol. Biol. 98 (1975), 503, Proc. Natl. Acad. Sci. USA 76 (1979) 368 3). Particularly suitable hybridization conditions are 5–6× SSC at 42° C.–60° C. and an incubation period of 1 to 20 hours, preferably 1 hour. Particularly suitable washing conditions are 0.1–0.5× SSC at 65° C.–70° C. and an incubation period of 15 minutes to 2 hours, preferably 30 minutes. To carry out the determination it is however also possible to choose other conditions since the optimal conditions are dependent on the type and concentration of the probe and on the nucleic acid to be determined. Thus for example a lower hybridization temperature can be used by addition of 40% formamide. Likewise an organic solvent at a concentration of up to 50%, preferably 20 to 50%, can be added. Suitable hybridization conditions may be calculated, as described in Anal. Biochem. 178 (1984) 267, from the length of the probe, salt content of the reagent, GC content of the probe and temperature. The following conditions have proven to be particularly suitable:

GC content of the probe 43%–60%, length of the probe at least 27 nucleotides, hybridization at 42° C.–60° C. and at 5–6× SSC for 1 hour, wash at 65° C.–70° C. and at 0.1–0.5× SSC for 30 minutes, by addition, if desired, of 40% to 50% denaturing agent (e.g. formamide) during the hybridization.

1× SSC is understood as an aqueous solution of
0.15 mol/l NaCl
0.015 mol/l $Na_3$ citrate×2 $H_2O$,
which has been adjusted to pH 7 with 1 mol/l HCl. Items such as 0.1× SSC are corresponding dilutions of this solution.

Membranes or carrier materials based on nitrocellulose are suitable as carriers (e.g. Schleicher and Schell BA85, Amersham Hybond C), reinforced or bound nitrocellulose in powder form or nylon membranes derivatized with various functional groups (e.g. nitro group) (e.g. Schleicher and Schell Nytran, NEN Gene Screen, Amersham Hybond N, Pall Biodyne). Before carrying out the determination the carrier is preferably pretreated in order to prevent non-specific binding of the probes to the carrier. Blocking substances suitable for the pre-hybridization are for example phosphate buffered saline with bovine serum albumin, non-ionic detergents, polyanions and DNA from herring sperm. Nitrocellulose filters and nylon membranes are preferably pretreated with 5× SSC at 65° C. for 1 hour.

After carrying out the incubation the carrier is washed in order to remove unhybridized nucleic acids. This can be effected for example by a solution of 0.1–1% (v/v) of an ionic detergent with addition, if desired, of a salt (e.g. sodium chloride or sodium citrate) or with SSC preferably 0.1–0.5× SSC.

When using radioactively labelled probes autoradiography is carried out.

When using probes labelled with hapten, incubation is with an antibody or antibody fragment against the hapten. The antibody thereby carries a label such as a radioactive or enzyme label. After the incubation with the antibody it is washed again in order to detect only those antibody conjugates which are bound specifically. The determination is then carried out via the label of the antibody or the antibody fragment according to well-known methods. An analogous procedure applies for a biotin or avidin label.

The labelling of the anti-hapten antibody or the antibody fragment is carried out according to well-known methods. Suitable are e.g. an enzyme label, radioactive label, (bio)luminescent label or fluorescent label. An enzyme label is however preferably used with enzymes such as alkaline phosphatase, peroxidase or β-galactosidase. Particularly preferred as the enzyme label is alkaline phosphatase. The determination of alkaline phosphatase is carried out via leuco systems, especially via indigoid systems as oxidizable compounds (cf. EP-A 0228663). Tetrazolium salts serve as oxidizing agents. For the enzyme label alkaline phosphatase X-phosphate/nitroblue-tetrazolium is preferably used as the redox system (F. P. Altmann, Tetrazolium salts and Formazans, Progr. Histochem. Cytochem. Vol. 913 (1976), Gustav-Fischer-Verlag Stuttgart, page 1). In this connection, X-phosphate is understood as 5-bromo- 4-chloro-3-indolylphosphate and nitroblue-tetrazolium as 3,3'-(3,3'-dimethoxy-4,4'-biphenylene)-bis-5-phenyl- 2-(4-nitrophenyl)-tetrazolium chloride. Alkaline phosphatase cleaves the chromogenic substrate (X-phosphate) which forms a blue, sparingly soluble dimer by cleavage of the phosphate and oxidation which simultaneously reduces the tetrazolium compound to a likewise blue, sparingly soluble formazan.

The detection of the other suitable labelling systems is carried out according to well-known methods.

A further embodiment of the invention is a reagent for the determination of listeriosis which is characterized in that it compromises a labelled nucleic acid which has a length of at least 27 nucleotides and which hybridizes at 5–6× SSC and 42° C.–60° C. with the 2.5 kb large KpnI-BamHI fragment from the plasmid pLM63 (DSM 5220). A reagent is preferred which contains a labelled nucleic acid which hybridizes with a nucleic acid according to FIG. 1 under the conditions mentioned above. Also preferred is a reagent which contains a labelled nucleic acid which hybridizes with a nucleic acid corresponding to the nucleotides 822–1890 of FIG. 1 under the above-mentioned conditions. The hybridization period is preferably 1–20 hours, particularly preferred is 1 hour. Furthermore the reagent contains a detection system for the label. The above mentioned procedures can be used for the labelling.

A labelled nucleic acid corresponding to the sequence of FIG. 1 or corresponding to nucleotides 1–714, 822–1890, 935–1244, 1158–1185 or 1209 to 1718 is preferably used.

A further embodiment of the invention is a protein which is at least 80% homologous to the amino acid sequence of protein I, protein II or protein III cited in FIG. 1 III. A protein is preferred which is at least 80% homologous to protein II. This protein has a molecular weight of 18 kD. The proteins are suitable for the production of antibodies against Listeria. The proteins with the amino acid sequence according to FIG. 1 or the partial sequences protein I, protein II or protein III are preferred. Particularly preferred is protein II.

With the protein according to the present invention, which is modified if desired, antibodies and antisera against pathogenic Listeria bacteria can be obtained by immunizing experimental animals, collecting antiserum and purifying the antibodies according to well-known procedures. Monoclonal antibodies can be obtained by immunizing experimental animals with protein in accordance with the present invention which is modified if desired, fusing B-lymphocytes of the immunized animals thus obtained with transforming agents, cloning and culturing the hybrid cells thus formed which produce the monoclonal antibody and isolation of the latter. Rats and mice are particularly suitable animals for the production of antibodies. Suitable modifying agents are for example N-bromo-succinimide (NBS) by oxidation of tryptophan groups on the protein (BBA 143 (1967) 462–472) carboxymethylation with iodoacetate (IAA) which mainly attacks histidine or nitration with tetranitromethane (TNM) (J. Biol. Chem. 238 (1963) 3307) as well as diazotization with diazotized sulphanilic acid (Meth. Enzymol. 25 (1972) 515–531). Balb/c mice or AJ mice are particularly suitable as the experimental animals.

The immunization is carried out by the usual administration of the native or modified enzyme preferably in combination with an adjuvant. Freund's adjuvant or aluminium hydroxide together with Bordetella pertussis are preferably used as the adjuvant. The immunization is usually carried out for at least 2 and preferably for 4 months.

In order to isolate monoclonal antibodies the B-lymphocytes of the immunized animals are fused with transforming agents according to the usual methods. Examples of transforming agents used within the scope of the present invention, are myeloma cells, transforming viruses such as e.g. Epstein-Barr virus or agents which are described in DE-A 32 45 665. The fusion is carried out according to the well-known procedure of Köhler and Milstein (Nature 256 (1975) 495–497). The hybrid cells which form in this process are cloned in the usual manner e.g. by use of a commercial cell sorter and the clones obtained which form the desired monoclonal antibodies are cultured. The production and selection of monoclonal antibodies is for example described in detail in J. Immunol. Meth., 39 (1980) 285–308.

A further embodiment of the invention is an immunological method for the determination of Listeria bacteria in which at least one monoclonal or, if desired, polyclonal antibody is used against the protein according to the present invention. In principle all current immunoassays such as e.g. radioimmunoassay, enzyme-immunoassay, fluorescence-immunoassay etc. are suitable as immunological determination methods. Furthermore all variants of the procedures such as e.g. the competitive immunoassay IEMA method can be used. The usual agents for the respective determination method are suitable for the labelling. Thus radio-isotopes, for example $^{125}$I are used for the labelling in a radioimmunoassay. For an enzyme-immunoassay all the enzymes which are usually used, such as for example peroxidase or β-galactosidase, are suitable. For a fluorescence immunoassay the usual fluorescent groups can be used as the label. Details of these various test methods and variants of the procedures are known to the expert.

In the determination method the monoclonal or polyclonal antibodies as such or fragments thereof can be used which have the corresponding immunological properties for example Fab fragments.

The following Examples and the Figures elucidate the invention further. The quoted percentages are percentages by weight unless stated otherwise. FIG. 1 shows the DNA sequences of dth 18 (nucleotide 822–1890) and of a preferred section of the 2.5 kb large KpnI-BamHI fragment of plasmid pLM63 (nucleotide 1–1890) as well as the amino acid sequences of proteins I, II and III including the start codon.

EXAMPLE 1

Labelling of the DNA probes 200 ng of the isolated DNA are labelled with $^{32}$P as described in Anal. Biochem. 132 (1983), 6–13.

EXAMPLE 2

Preparation of the samples 2.1 Microorganisms

The strains used as a reference are listed in Tab. Ia. All the other Listeria strains (Tables Ib, II) were chosen from a collection of about 3000 Listeria strains of the National Institute of Public Health and Environmental Protection, Bildhoven. Among the strains examined are 40 strains which originate from patients who suffer from listeriosis. These strains were isolated as described in Zbl. Bact. I Abt. Orig. A 246 (1980), 211–227. The microorganisms were cultured for 24 hours at 30° C. in a liquid selection and enrichment medium (pH 7.0, 1 g/l peptone, 8.5 g/l NaCl, 10 µg/ml trypaflavin.HCl, 10 µg/ml nalidixic acid, 50 µg/ml cycloheximide) and subsequently plated on a special nutrient medium (enrichment medium+1% agar). After incubation at 30° C. for 24 hours these plates are used directly in the hybridization test.

2.2 Other sample material

Cerebrospinal fluid, feces, blood, lochia, brain material, liver, cervical material, amniotic fluid, food, silage grass and animal material are used as additional sample material. 20 g of this material is suspended in 250 ml phosphate buffered saline, homogenized and further processed as described in International Journal of Food Microbiology 4 (1987), 249–256.0.1 ml sample is plated on non-selective agar plates (85 mm in diameter) and incubated overnight.

2.3 Procedure for a hybridization test with a DNA probe (dth 18, 1069 nucleotides or pLM63, 1890 nucleotides, FIG. 1)

A replica of the plates prepared according to 2.1 or 2.2 was made onto nylon membranes (Gene Screen Plus Membranes®, DuPont Corp., U.S. Pat. No. 4,455,370) The membranes are placed on filter paper which is saturated with 0.5 mol/l NaOH and incubated for 5 minutes in a boiling water-bath. Afterwards the membranes are placed on filter paper which is saturated with 1 ml 0.5 mol/l of fresh NaOH and neutralized with 1 ml 1 mol/l Tris buffer (pH 7.5). This neutralization step is repeated. The membranes are dipped in 100 ml 5× SSC and at the same time the cell residues are rubbed off with a cloth. After drying in air the membranes are prehybridized with 15 ml solution A for 6 to 16 hours at 40° C. Afterwards the DNA probe dth 18 or pLM63 (0.05 μg in 2.5 ml, 5× SSC) is added and incubated for 18 hours at 60° C. Afterwards they are washed for 45 min in a water-bath at 65° C. with 0.2× SSC which contains in addition 1% SDS and 0.1% sodium pyrophosphate. After drying, the membranes are shrink-wrapped in plastic foil and an X-ray film is exposed with them for 18 hours at −70° C.

2.4 Hybridization with a 314 bp DNA probe

Hybridization tests are carried out with a shortened probe (nucleotide 1209–1718 (cf. FIG. 1). The conditions for the hybridization are 5× SSC at 42° C. (1 hour) and subsequent washing in 0.2× SSC at 70° C. (30 minutes). It can be seen that this probe is also suitable as a DNA probe to test for listeriosis.

Reagents:
1× SSC: 0.15 mol/l NaCl and 0.015 mol/l sodium citrate
Solution A:
50 mmol/l Tris buffer, pH 7.5
10 mmol/l EDTA
1 mol/l NaCl
0.2% Ficoll
0.2% polyvinylpyrrolidone
0.2% bovine serum albumin
1 mg/ml denatured DNA from herring sperm
1% sodium pyrosphate and
10% SDS (sodium dodecyl sulphate).

For the further examinations less stringent conditions (2× SSC at 65° C.) were used. Analogous results were thus obtained.

EXAMPLE 3

Comparative experiments with a DNA probe according to the state of the art (listeriolysin 0)

A synthetic 19 mer-oligomer ($^5$GATCACTCTGGAG-GATACG$^3$) was used as the probe (analogous to Infection and Immunity 56 (1988), 766–772).

200 ng of this DNA probe was labelled at the 5'-end with $^{32}$P as described in Maxam and Gilbert (Meth. Enzymol. 65 (1980), 499).

The hybridization conditions were: 6× SSC at 37° C., washing three times with 6× SSC containing 1% SDS and 0.1% sodium pyrophosphate at 40° C. for 30 min each.

EXAMPLE 4

Determination of the biotype of the microorganisms used

The determination of the biotype was carried out as described in An. Inv. Pasteur/Microbiol. 134 (1983) 56–71. The strains were cultured for two days at 37° C. in 4 ml semisolid peptone-agar medium which contained 1% D-xylose or L-ramnose. The peptone medium consists of 10 g bacto-peptone, 5 g sodium chloride, 5.5 oxoidagar L 28 and 0.08 g bromthymol blue dissolved in 1000 ml distilled water, pH 7.8 autoclaved at 120° C. for 15 min. After the autoclaving, filter-sterilized sugar solution was added up to a final concentration of 1%. In order to determine the biotype haemolysin production was examined by growing the strains overnight at 37° C. in brain heart infusion broth. 0.2 ml are withdrawn from this culture and added to 0.2 ml of a 2% suspension of sheep erythrocytes in PBS (phosphate buffered saline) which was washed three times. After incubation for two hours at room temperature it is tested for haemolysis. *L. monocytogenes*, NCTC7973 and *L. innocua*, NCTC11289 served as the positive and negative controls. The determination of the biotype was carried out according to Zbl. Bakt. Mikrobiol. Hyg. I Abt. Orig. A 259 (1985) 341–350.

EXAMPLE 5

Determination of the serotype

The determination of the serotype was carried out as described in Seeliger and Höhne (Zbl. Bact. Microbiol. Hyg. I Abt. Orig. A, 259 (1985), 341–350).

The strains were cultured in 4 ml tryptone phosphate broth, enriched with 1% glucose and shaken for 6–7 hours at 37° C. in a water-bath. A tryptose-agar plate is inoculated with this culture and incubated overnight at 37° C. Parallel to this a second tube containing tryptose phosphate broth to which 1% glucose was added, is inoculated and incubated and shaken overnight at 25° C. in a water-bath. The tryptose phosphate plate is harvested with 5 ml phosphate buffered saline, pH 7.4 and heated for one hour in a boiling water-bath and subsequently centrifuged.

The cells are resuspended and adjusted to a concentration of $5\times10^8$ cells/ml ($1\times10^9$ cells/ml have an OD of 1.0 at 600 nm). 0.2 ml are withdrawn from this suspension and added to 0.2 ml of a 75-fold dilution of antiserum against the polysaccharide antigens I, II, V, VI, VIII and IX in a glass tube and incubated for 2 hours at 45° C. Afterwards it is cooled and incubated overnight at 4° C. Afterwards the tubes are tested for visible agglutination.

The determination of the serotype is carried out as described in detail in Bergey's Manual of Bacteriology (N. R. Kreig, J. G. Holt (eds) Bergeys Manual of Systematic Bacteriology (1984), Williams and Wilkins, Baltimore and London). The serotype was classified into the classes 1/2a, 1/2b, 1/2c, 3a, 3b, 3c, 4a, 4b, 4d, 4a/b, 5, 6b and 7.

EXAMPLE 6

Mouse bioassay

A mouse bioassay (as described in Infect. Immun. 45 (1984), 234–241) is carried out in order to examine whether a Listeriosis strain is pathogenic. For this the mouse is injected intravenously with $10^4$–$10^5$ bacteria in 200 μl phosphate buffered saline pH 7.4. After 2–4 days the mice are killed and the spleen is removed. A strain is denoted pathogenic when the number of bacteria found in the whole spleen exceeds $10^4$.

EXAMPLE 7

Preparation of Listeria antibodies

50 μg of the purified antigen (amino acid sequence Table III) in complete Freund's adjuvant is injected intramuscularly (IM). The injection is repeated after three weeks, after 30 days and after 40 days. 10 days after the last injection antiserum is isolated and purified by affinity chromatography.

An immunoblot can be carried out with this antiserum for the determination of Listeria.

EXAMPLE 8

Examination of the suitability of a probe for the determination of Listeria

*E. coli* HB 101 (DSM 1607) are transformed with a plasmid based on pUC18 which contains as an insert the DNA sequence according to FIG. 1 and cultured overnight in the presence of 50 μg/ml ampicillin up to an optical density of OD 600 nm=1. 0.1 ml of this culture broth is plated on agar plates which contain 50 µg/ml ampicillin (85 mm in diameter) and incubated overnight.

A replica is made of the plates thus produced using nylon membranes (Gene Screen Plus-Membranes®, DuPont).

The membranes are placed on filter paper which is saturated with 0.5 mol/l NaOH and incubated for 5 minutes in a boiling water-bath. Afterwards the membranes are placed on filter paper which is saturated with 1 ml 0.5 mol/l of fresh NaOH and neutralized with 1 ml 1 mol/l Tris buffer (pH 7.5). This neutralization step is repeated. The membranes are dipped in 100 ml 5× SSC and at the same time the cell debris are rubbed off with a cloth. After drying in air the membranes are pre-hybridized with 15 ml solution A for 6 to 16 hours at 40° C. Afterwards the DNA probe which is to be examined for its suitability (0.05 µg in 2.5 ml) is added and incubated for 18 hours at 60° C. Afterwards they are washed for 45 min in a water-bath at 65° C. with 0.2× SSC which contains in addition 1% SDS and 0.1% sodium pyrophosphate. After drying, the membranes are shrink-wrapped in plastic foil and an X-ray film is exposed with them for 18 hours at −70° C. If signals are visible on the X-ray film which originate from a hybridization, this probe is suitable for use in the listeriosis test. When plasmid pLM63 (DSM 5220) is used analogous results are obtained.

EXAMPLE 9

Comparison of the hybridization of a probe according to the present invention and a reference probe (cf. Example 3) with various Listeriosis strains. The hybridization was carried out as described in Examples 2 and 3. The results are shown in Table I and II.

TABLE I

Comparison of the hybridization of a DNA probe according to the present invention (1) (935 bp to 1244 bp of FIG. 1) and a DNA probe according to the state of the art (listeriolysin 0, (2), prepared according to Example 3) with DNA from Listeria strains.

Analogous results are obtained with nucleotides 1–714 as DNA probe (1). This probe hybridizes in addition with DNA from Listeria monocytogenes strains of the serotype 4a (e.g. NCTC 5214).

TABLE Ia

| | with reference strains | | | |
|---|---|---|---|---|
| Sero- | | | probe | |
| type | Strain No.[1] | Biotype | 1 | 2 |
| 1/2 a | NCTC7973 | L.monocytogenes | + | + |
| 1/2 b | SLCC2755 | L.monocytogenes | + | + |

TABLE Ia-continued

| | with reference strains | | | |
|---|---|---|---|---|
| Sero- | | | probe | |
| type | Strain No.[1] | Biotype | 1 | 2 |
| | SLCC3954 | L.seeligeri | − | − |
| 1/2 c | NCTC5348 | L.monocytogenes | + | + |
| 3 a | NCTC5105 | L.monocytogenes | + | + |
| 3 b | SLCC2540 | L.monocytogenes | + | + |
| 3 c | SLCC2479 | L.monocytogenes | + | + |
| 4 b | NCTC10527 | L.monocytogenes | + | + |
| 4 c | ATCC19116 | L.monocytogenes | + | + |
| 4 d | NCTC10888 | L.monocytogenes | + | + |
| 4 e | ATCC19118 | L.monocytogenes | + | + |
| 4 ab | NCTC10528 | L.monocytogenes | + | + |
| 5 | ATCC19119 | L.ivanovii | + | − |
| 6 a | SLCC 5334 | L.welshimeri | − | − |
| | NCTC11288 | L.innocua | − | − |
| 6 b | NCTC11289 | L.innocua | − | − |
| 7 | SLCC 2482 | L.monocytogenes | + | + |
| | RIVM 1 | L.grayi | − | + |
| | RIVM 2 | L.murrayi | − | + |

[1]Repositories cf. World Directory of Collections of Cultures of Microorganisms edited by V.F. McGowan and V.B.D. Sherman, World Data Center, University of Queensland, Australia, 1982.

TABLE Ib

| | with a multitude of strains | | | |
|---|---|---|---|---|
| Number of strains | | | probe | |
| examined | Biotype | | 1 | 2 |
| 34 | L.monocytogenes | (34) | 34 | 34 |
| 39 | L.monocytogenes | (37) | 37 | 37 |
| | L.seeligeri | ( 1) | 0 | 0 |
| | L.welshimeri | ( 1) | 0 | 0 |
| 16 | L.monocytogenes | (16) | 16 | 16 |
| 5 | L.monocytogenes | ( 5) | 5 | 5 |
| 5 | L.monocytogenes | ( 3) | 3 | 3 |
| | L.welshimeri | ( 1) | 0 | 0 |
| | L.seeligeri | ( 1) | 0 | 0 |
| 2 | L.monocytogenes | ( 1) | 1 | 1 |
| | L.innocua | ( 1) | 0 | 0 |
| 77 | L.monocytogenes | (77) | 76 | 76 |
| 5 | L. seeligeri | ( 5) | 0 | 0 |
| 2 | L.monocytogenes | ( 2) | 2 | 2 |
| 1 | L.monocytogenes | ( 1) | 1 | 1 |
| 34 | L.innocua | (32) | 0 | 1 |
| | L.welshimeri | ( 2) | 0 | 0 |
| 23 | L.innocua | (18) | 0 | 2 |
| | L.welshimeri | ( 5) | 0 | 0 |
| 7 | L.monocytogenes | ( 7) | 7 | 7 |
| 2 | L.grayi | ( 2) | 0 | 2 |
| 3 | L.murrayi | ( 3) | 0 | 3 |

TABLE II

Table II shows the hybridization reaction of probe 1 with various Listeria strains whose pathogenicity was determined according to Example 6.

| | Sero- | | Hybridi- | log No./g spleen | |
|---|---|---|---|---|---|
| Biotype | type | Origin | zation | 2nd Day | 4th Day |
| L.monocytogenes | 1/2 a | reference strain | + | 7.4[c] | 8.3+ |
| L.monocytogenes | 1/2 b | soft | + | 6.2 | 7.1+ |

TABLE II-continued

Table II shows the hybridization reaction of probe 1 with various Listeria strains whose pathogenicity was determined according to Example 6.

| Biotype | Serotype | Origin | Hybridization | log No./g spleen 2nd Day | 4th Day |
|---|---|---|---|---|---|
| L.monocytogenes | 1/2 c | cheese food | + | 5.4 | ++ |
| L.monocytogenes | 3 a | food | + | 6.4 | 6.5 |
| L.monocytogenes | 3 b | food | + | 8.4 | ++ |
| L.monocytogenes | 3 c | food | + | 8.2 | ++ |
| L.monocytogenes | 4 b | soft cheese | + | 7.0 | ++ |
| L.monocytogenes | 4 b | soft cheese | + | 6.5 | ++ |
| L.monocytogenes | 4 b | soft cheese | + | 8.3 | ++ |
| L. seeligeri | 4 c | food | − | <2.0 | <2.0 |
| L.innocua | 6 a | soft cheese | − | 2.0 | 3.7 |
| L.innocua | 6 b | soft cheese | − | <2.0 | <2.0 |
| L.grayi | | reference strain | − | <2.0 | <2.0 |
| L.murrayi | | reference strain | − | <2.0 | <2.0 |

[a] $10^4$–$10^5$ organisms were injected into 4 mice.
[b] Hybridization is carried out with the dth 18 gene as probe (cf. Example 2.3).
[c] Mean of two mice;
+: Mouse died before sampling.

It will be understood that the specification and examples are illustrative but not limitative of the present invention and that other embodiments within the spirit and scope of the invention will suggest themselves to those skilled in the art.

We claim:

1. An isolated nucleic acid molecule, which is at least 27 nucleotides in length, is a nucleotide sequence specific for pathogenic strains of Listeria bacteria and which hybridizes to the nucleotide sequence of FIG. 1 or to the complementary nucleotide sequence of that shown in FIG. 1 at 5–6× SSC and 42°–60° C. and washing for at least 30 minutes at from 0.1–0.5× SSC and at a temperature of from 65° C.–70° C.

2. The isolated nucleic acid of claim 1, wherein said nucleic acid molecule has a GC content of 43% to 60%.

3. The isolated nucleic acid of claim 1 further comprising a label.

4. The isolated nucleic acid of claim 3, wherein said label is radioactive, biotin, avidin, streptavidin, a fluorescent dye or a hapten.

5. The isolated nucleic acid of claim 1 which hybridizes to the nucleotide sequence of FIG. 1 or to the complementary nucleotide sequence of FIG. 1.

6. An isolated nucleic acid molecule useful in identifying pathogenic strains of Listeria bacteria, the isolated nucleic acid molecule selected from the group consisting of nucleotides 1 to 714 and nucleotides 935 to 1244 of FIG. 1.

7. The isolated nucleic acid molecule of claim 6 consisting of nucleotides 1 to 714 of FIG. 1.

8. The isolated nucleic acid molecule of claim 6 consisting of nucleotides 935 to 1244 of FIG. 1.

9. A hybridization method for identifying the presence of pathogenic strains of Listeria bacteria in a biological sample comprising: a. Isolating nucleic acid from the sample;

b. Assaying said nucleic acid for the presence of a DNA sequence corresponding to the nucleotide sequence of FIG. 1 or the complementary nucleotide sequence of FIG. 1, thereby determining the presence of a pathogenic strain of Listeria bacteria.

10. Method of claim 9 comprising hybridization at 5–6× SSC and at a temperature of from 42°–60° C. and a washing step at 0.1–0.5× SSC for at least 30 minutes at a temperature of from 65° C. to 70° C.

* * * * *

UNITED STATES PATENT AND TRADEMARK OFFICE
CERTIFICATE OF CORRECTION

PATENT NO. : 5,550,022
DATED : August 27, 1996
INVENTOR(S) : Chakraborty et al

It is certified that error appears in the above-identified patent and that said Letters Patent is hereby corrected as shown below:

Title Page, under the section entitled Related U.S. Application Data,
Line 2, change "Oct. 15, 1990," to read as -- Sept. 7, 1990, --.

Title Page, under the section entitled Foreign Application Priority Data,
Line 1, change "39 01 397.9" to read as -- P 39 01 397.9 --.

Title Page, under the section entitled Foreign Application Priority Data,
Line 2, change "39 06 832.3" to read as -- P 39 06 832.3 --.

Title Page, under the section entilted Abstract, insert before the 1st line,
the sentence, "Method for the determination of Pathogenic Listeria Bacteria."

Column 2,
Line 16, change "pPLM63," to read as -- pPLM(63), --.
Line 21, change "nucleotide" to read as --nucleotides --.

Column 3,
Line 19, change "shorter fragments" to read as -- shorter chain fragments --.
Line 67, change "Schell" to read as -- Schüll --.

Column 4,
Line 4, change "Schell" to read as -- Schüll --.

Column 5,
Line 9, change "FIG. 1III." to read as --Figure 1. --.

UNITED STATES PATENT AND TRADEMARK OFFICE
CERTIFICATE OF CORRECTION

PATENT NO. : 5,550,022
DATED : August 27, 1996
INVENTOR(S) : Chakraborty et al

It is certified that error appears in the above-identified patent and that said Letters Patent is hereby corrected as shown below:

Column 6,
Line 59, insert a period in "4,455,370) The" to read as -- 4,455,370). The --.

Column 8,
Line 30, insert an apostrophe in "Bergeys" to read as -- Bergey's --.

Column 9,
Line 40, change "nucleotides" to read as -- nucleotide --.

Signed and Sealed this

Twenty-sixth Day of June, 2001

*Attest:*

*Attesting Officer*

NICHOLAS P. GODICI
*Acting Director of the United States Patent and Trademark Office*